US011134862B2

(12) United States Patent
Crawford et al.

(10) Patent No.: US 11,134,862 B2
(45) Date of Patent: Oct. 5, 2021

(54) METHODS OF SELECTING SURGICAL IMPLANTS AND RELATED DEVICES

(71) Applicant: GLOBUS MEDICAL, INC., Audubon, PA (US)

(72) Inventors: Neil Crawford, Chandler, AZ (US); Andrew Davison, Downingtown, PA (US); David Demski, Audubon, PA (US); Peter Govey, Philadelphia, PA (US); Norbert Johnson, North Andover, MA (US); Stephanie Wolfe, Hatfield, PA (US)

(73) Assignee: Globus Medical, Inc., Audubon, PA (US)

( * ) Notice: Subject to any disclaimer, the term of this patent is extended or adjusted under 35 U.S.C. 154(b) by 432 days.

(21) Appl. No.: 15/809,110

(22) Filed: Nov. 10, 2017

(65) Prior Publication Data

US 2019/0142304 A1 May 16, 2019

(51) Int. Cl.

| | |
|---|---|
| ***A61B 34/10*** | (2016.01) |
| ***A61B 5/107*** | (2006.01) |
| ***A61B 17/80*** | (2006.01) |
| ***A61B 34/00*** | (2016.01) |

(Continued)

(52) U.S. Cl.

CPC .............. *A61B 5/107* (2013.01); *A61B 17/80* (2013.01); *A61B 34/25* (2016.02); *G16H 30/00* (2018.01); *A61B 2017/568* (2013.01); *A61B 2034/108* (2016.02); *A61F 2250/0064* (2013.01); *A61F 2250/0078* (2013.01)

(58) Field of Classification Search

CPC .............. A61B 34/25; A61B 2034/102; A61B 2034/108; A61B 5/107; A61B 5/1072

See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,354,314 A | 10/1994 | Hardy et al. |

(Continued)

FOREIGN PATENT DOCUMENTS

| | | |
|---|---|---|
| EP | 1571581 A1 | 9/2005 |
| JP | 2006594 A | 1/2006 |

OTHER PUBLICATIONS

US 8,231,638 B2, 07/2012, Swarup et al. (withdrawn)

*Primary Examiner* — Anu Ramana

(57) ABSTRACT

Methods may be provided to identify a medical implant from a plurality of medical implants to be fixed to an anatomical surface. Dimensional parameters for each of the plurality of medical implants may be provided, and dimensional parameters corresponding to the anatomical surface may be provided. The dimensional parameters for each of the plurality of medical implants may be compared with the dimensional parameters corresponding to the anatomical surface, and one of the medical implants may be selected from the plurality of medical implants based on comparing the dimensional parameters for each of the plurality of medical implants with the dimensional parameters corresponding to the anatomical surface. An identification of the medical implant selected from the plurality of medical implants may be provided through a user interface. Related devices and computer program products are also discussed.

12 Claims, 10 Drawing Sheets

(51) Int. Cl.
*G16H 30/00* (2018.01)
*A61B 17/56* (2006.01)

(56) References Cited

U.S. PATENT DOCUMENTS

| | | | |
|---|---|---|---|
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |
| 7,683,331 | B2 | 3/2010 | Chang |
| 7,683,332 | B2 | 3/2010 | Chang |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,711,406 | B2 | 5/2010 | Kuhn et al. |

(56) References Cited

U.S. PATENT DOCUMENTS 7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Williams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,263,933 B2 7/2012 Hartmann et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.
8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena

(56) References Cited

U.S. PATENT DOCUMENTS 8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Issacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,241,724 B2 * 1/2016 Lang ......................... A61F 2/38
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 11/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.

(56) References Cited

U.S. PATENT DOCUMENTS

2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 von Jako
2008/0109012 A1 5/2008 Falco et al.
2008/0144906 A1 6/2008 Allred et al.
2008/0161680 A1 7/2008 von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0019884 A1* 1/2011 Blau .................. A61B 17/1725
382/128
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.

(56) References Cited

U.S. PATENT DOCUMENTS

2014/0121676 A1 5/2014 Kostrzewski et al.
2014/0128882 A1 5/2014 Kwak et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0130810 A1 8/2014 Azizian et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Mallet et al.
2015/0039034 A1 2/2015 Frankel et al.
2015/0085970 A1 3/2015 Bouhnik et al.
2015/0088293 A1 3/2015 Metzger
2015/0146847 A1 5/2015 Liu
2015/0150524 A1 6/2015 Yorkston et al.
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0273748 A1 9/2017 Hourtash et al.
2017/0296277 A1 10/2017 Hourtash et al.
2017/0360493 A1 12/2017 Zucher et al.

* cited by examiner

FIG. 8A
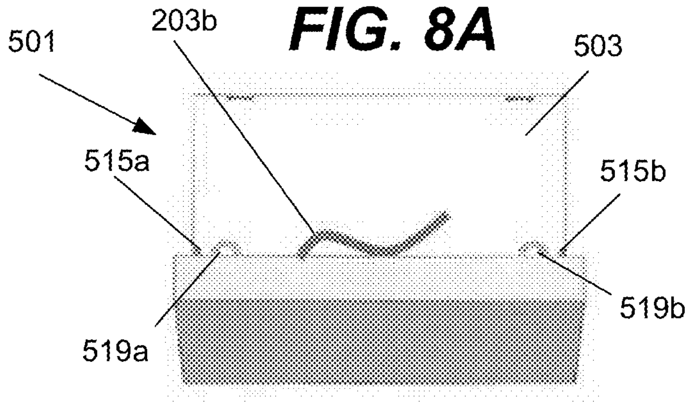
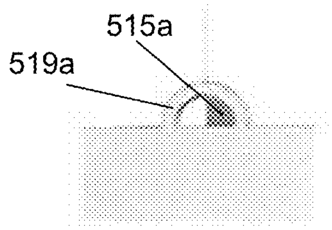
FIG. 8B
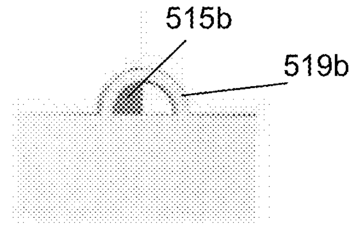
FIG. 8C
FIG. 9
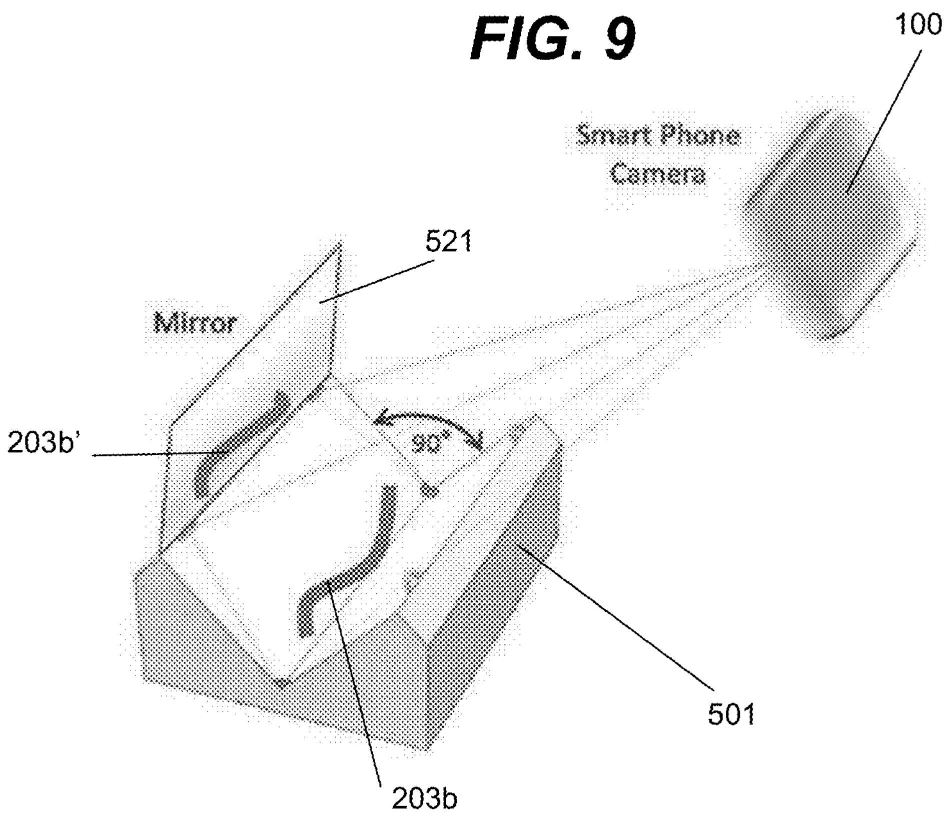

METHODS OF SELECTING SURGICAL IMPLANTS AND RELATED DEVICES

TECHNICAL FIELD

The present disclosure relates to medical procedures and, more particular, to medical implants and related methods, devices, and computer program products.

BACKGROUND

An orthopedic implant (such as a bone plate) may be used, for example, to support a damaged bone. The implant may be fabricated from stainless steel and/or titanium alloys, and a plurality of screw holes through the implant may allow fixation to the bone using bone screws. The surgeon may thus expose the damaged bone and screw the implant to the bone.

To facilitate variations in bone sizes and/or shapes, an implant for a particular bone may be manufactured in different sizes and/or shapes. The unique anatomy and injury pattern of each individual patient may thus require selection of a properly sized and contoured implant from a set of many available sizes and contours for the same type of implant. Positive treatment outcomes may correlate with well-fitting implants.

Accordingly, the surgeon may select from a number of implant sizes/shapes during surgery to fit the bone being repaired. The selection of a particular implant may involve the surgeon visually inspecting the exposed bone surface during surgery and selecting one or more of the implants based on the visual inspection. Selecting a best-fitting implant from among many implants may thus be a time-consuming and imprecise process for the surgeon, thereby increasing a time required to perform the surgery. Moreover, the surgeon may try to fit multiple implants to the bone before selecting the final implant resulting in waste due to contamination of implants that are tried but not used.

Accordingly, there continues to exist demand for improved methods of selecting orthopedic implants.

SUMMARY

Some embodiments of the present disclosure are directed to methods to identify a medical implant from a plurality of medical implants to be fixed to an anatomical surface. Dimensional parameters for each of the plurality of medical implants may be provided, and dimensional parameters corresponding to the anatomical surface may be provided. The dimensional parameters for each of the plurality of medical implants may be compared with the dimensional parameters corresponding to the anatomical surface, and one of the medical implants may be selected from the plurality of medical implants based on comparing the dimensional parameters for each of the plurality of medical implants with the dimensional parameters corresponding to the anatomical surface. An identification of the medical implant selected from the plurality of medical implants may be provided through a user interface. Related devices and computer program products are also discussed.

Other systems, methods, and computer program products according to embodiments of the inventive subject matter will be or become apparent to one with skill in the art upon review of the following drawings and detailed description. It is intended that all such additional systems, methods, and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

Other features of embodiments will be more readily understood from the following detailed description of specific embodiments thereof when read in conjunction with the accompanying drawings, in which:

FIGS. 8A, 8B, and 8C illustrate an image cradle and alignment markings thereof according to some embodiments of inventive concepts;

FIG. 9 is a diagram illustrating an image cradle with a mirror according to some embodiments of inventive concepts;

DETAILED DESCRIPTION

In the following detailed description, numerous specific details are set forth in order to provide a thorough understanding of embodiments of the present disclosure. However, it will be understood by those skilled in the art that the present invention may be practiced without these specific details. In other instances, well-known methods, procedures, components and circuits have not been described in detail so as not to obscure the present invention. It is intended that all embodiments disclosed herein can be implemented separately or combined in any way and/or combination.

Figure 1:
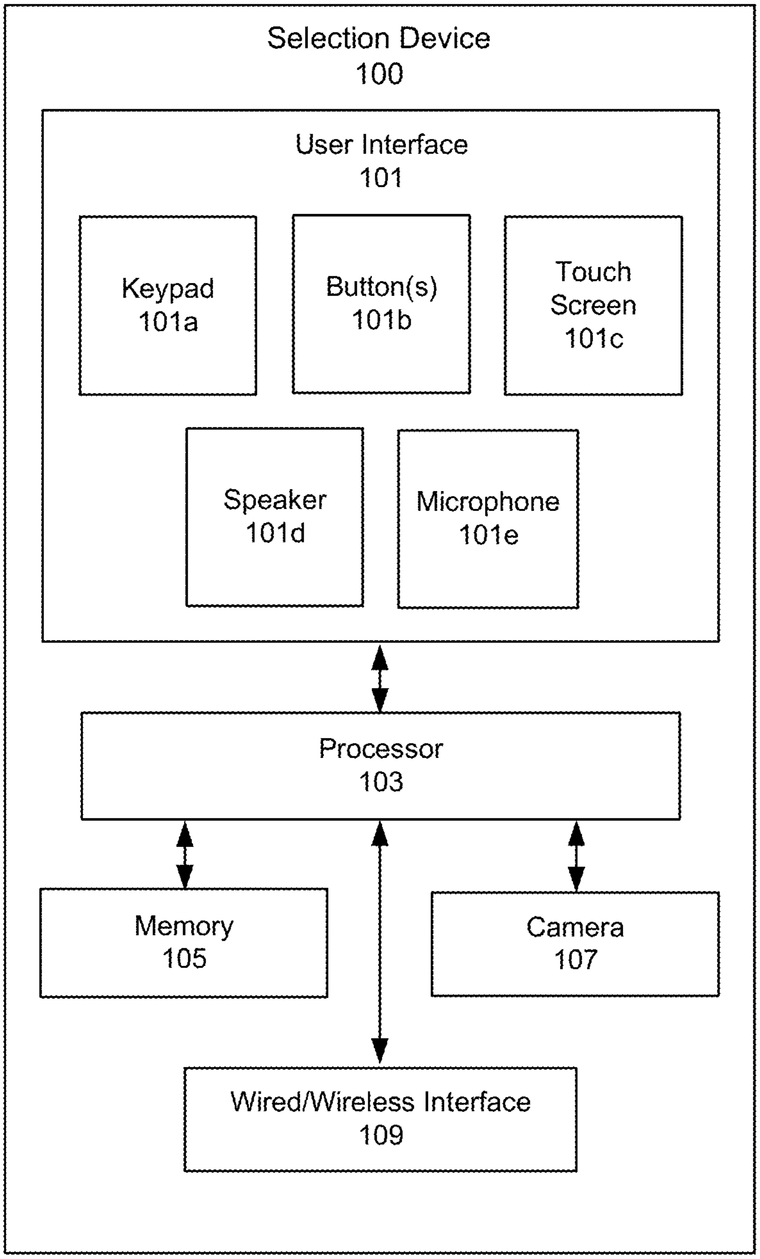
FIG. 1 is a block diagram illustrating a selection device according to some embodiments of inventive concepts.

FIG. 1 is a block diagram illustrating elements of selection device 100 configured to provide assistance in the selection of a medical implant (e.g., an orthopedic implant, such as a bone plate) according to some embodiments of inventive concepts. As shown, selection device 100 may include user interface 101, processor 103, memory 105, camera 107, and/or wired/wireless interface 109, and processor 103 may be coupled with each of user interface 101, memory 105, camera 107, and/or wired/wireless interface 109. Selection device 100 of FIG. 1, for example, may be implemented using a smartphone, a tablet computer, a laptop computer, a desktop computer, a dedicated computing device, etc., configured to perform operations to select an medical implant according to embodiments herein. Selection device 100, for example, may be a smartphone, tablet computer, laptop computer, or desktop computer running an app/software configured to perform operations discussed herein. According to some other embodiments, selection device 100 may be provided in/as a head mounted device worn by the surgeon. According to still other embodiments, selection device 100 may be integrated with other operating room equipment.

As discussed herein, operations of the selection device 100 of FIG. 1 may be performed by processor 103, user interface 101, wired/wireless interface 109, and/or camera 107. For example, processor 103 may accept data regarding the implant surface through camera 107 and/or wired/wireless interface 109, select one of a plurality of implants, and provide an identification of the selected implant through user interface 101. Moreover, modules may be stored in memory 105, and these modules may provide instructions so that when instructions of a module are executed by processor 103, processor 103 performs respective operations (e.g., operations discussed below with respect to FIG. 17). According to other embodiments, processor circuit 103 may be defined to include memory so that a separate memory is not required.

According to some embodiments, camera 107 may be used to capture images, where the images are used by processor 103 to provide/generate dimensional parameters corresponding to an anatomical surface (e.g., a bone surface) to which the implant (e.g., an orthopedic implant such as a bone plate) is to be fixed. According to some other embodiments, images or other data may be captured outside selection device 100 and received by processor 103 through wired/wireless interface 109, or dimensional parameters corresponding to the anatomical surface may be generated outside selection device 100 and received by processor 103 through wired/wireless interface 109, such that camera 107 may be omitted. Wired/wireless interface 109, for example, may include a wired interface (e.g., a Universal Serial Bus or USB port), a short range wireless interface (e.g., a BlueTooth transceiver, a WiFi transceiver, etc.), and/or a long range wireless interface (e.g., a cellular radio telephone transceiver).

As shown, user interface 101 may include one or more of a plurality of input/output devices. For example, keypad 101*a*, one or more buttons 101*b*, touch screen 101*c*, and/or microphone 101*e* may be provided to accept user input, and touch screen 101*c* and/or speaker 101*d* may provide user output (e.g., an identification of a selected medical input). According to some other embodiments, a conventional display (non-touch screen) may be used to provide user output with keypad 101*a* and/or button(s) 101*b* being used to accept user input. Camera 107, for example, may be operated responsive to user input through keypad 101*a*, button(s) 101*b*, touch screen 101*c*, and/or microphone 101*e*.

According to some embodiments of inventive concepts, methods, devices, and/or computer program products may be provided to log the unique morphology of an intended implant site (e.g., bone surface) intraoperatively and to apply best-fit algorithms to assist selection of a most suitable implant. For example, a best-fitting anatomically contoured bone plate may be selected from a plurality of bone plates according to some embodiments.

As discussed below with respect to FIGS. 2-11, a surgeon may use selection device 100 with the following operations of templating, imaging, and image analysis to select a particular implant from a plurality of implants of varying sizes and shapes/contours. While selection of a clavicle plate is discussed by way of example in the following embodiments, embodiments of inventive concepts may be applied for other medical/orthopedic implants and/or bone plates.

Figure 2A:
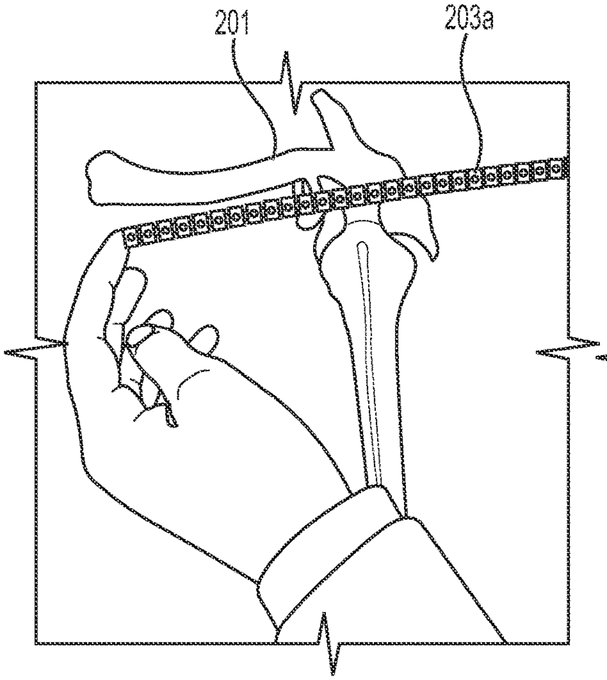
FIG. 2A illustrates a template material and FIG. 2B illustrates a template on a bone according to some embodiments of inventive concepts.
Figure 2B:
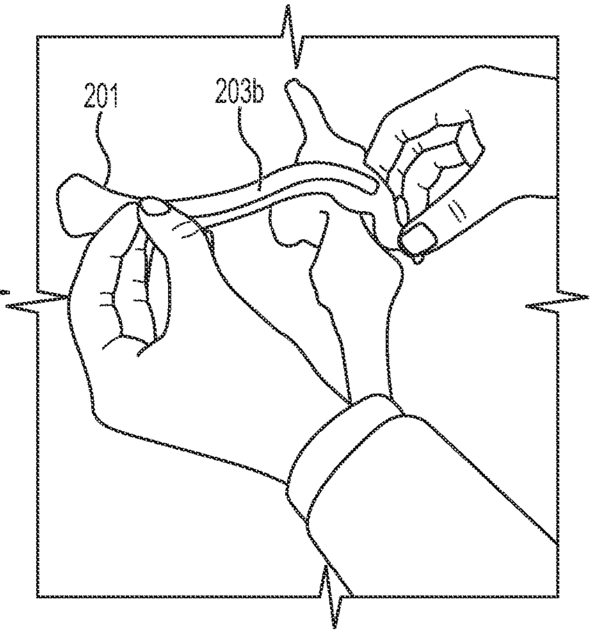

The surgeon may first surgically expose the site of intended plate fixation (e.g., a surface of clavicle 201), and then the surgeon may shape a malleable template to fit a 3-dimensional contour of the intended implant site. As shown in FIGS. 2A and 2B, a desired length of malleable template material 203*a* may be broken off (by hand) to represent a desired length of the implant, and the surgeon may shape the resulting malleable template 203*b* to fit a 3-dimensional contour of the exposed implant site as shown in FIG. 2B. The resulting shaped template 203*b* is shown in the two (substantially orthogonal) views of FIGS. 3A and 3B.

Figure 3A:
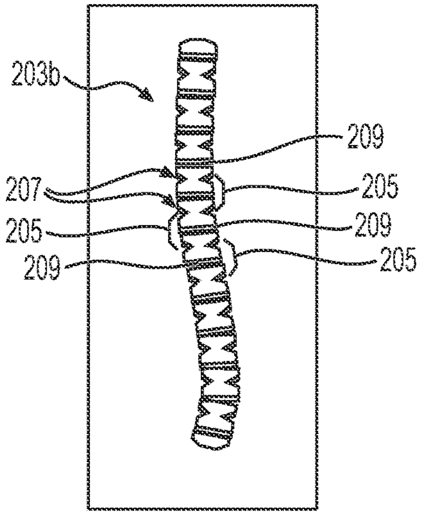
FIGS. 3A and 3B illustrate orthogonal views of the template of FIG. 2B according to some embodiments of inventive concepts.
Figure 3B:
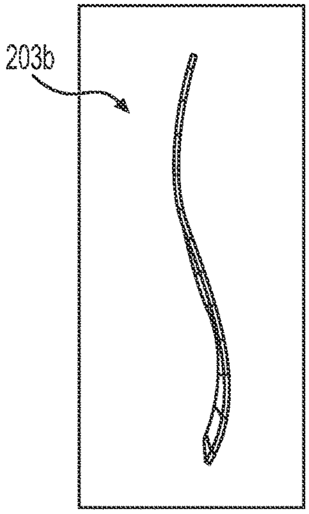

As shown in FIGS. 3A and 3B, the template 203*b* may have lengthwise segments 205 with lengths equal to the spacing between implant screw holes of the implant. The template material 203*a* may preferentially break at notches 207 between these segments, and each segment 205 may be marked with lines 209 perpendicular with respect to a trajectory of the segment. These lines 209 contrast with the template itself to facilitate image recognition. Lines 209 (or other markings) may be provided on only one of the two primary faces of the template to ensure reading of a proper orientation of the template (and not an inverted orientation). According to some embodiments, lines 209 may be provided on a face away from the bone to reduce obstruction of lines 209 due to blood or other material resulting from contact with the exposed bone. According to some other embodiments, lines 209 may be provided on a face adjacent to the bone so that the marked face of the template more closely matches the contour of the bone.

Figure 4A:
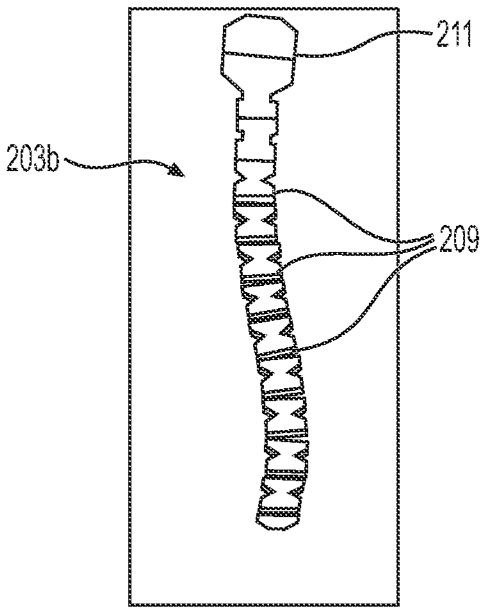
FIG. 4A illustrates a template and FIG. 4B illustrates a corresponding bone plate according to some embodiments of inventive concepts.
Figure 4B:
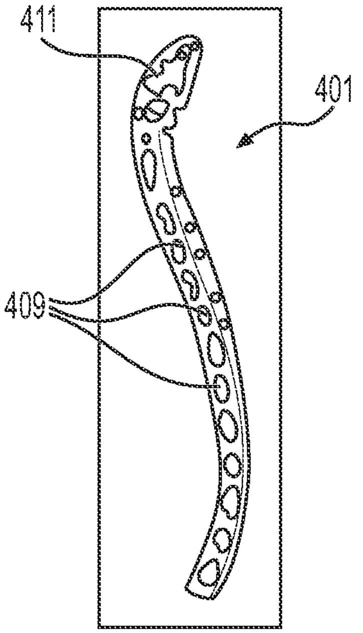

As shown in FIG. 4A, one end of template 203*b* may have a larger segment 211 to indicate/represent a specific end of the implant. For example, the larger segment 211 of FIG. 4A may represent a metaphyseal region 411 of bone plate 401 of FIG. 4B. This larger segment 211 of template 203*b* may alternatively be broken off if not wanted. In addition, lines 209 may be provided on template 203*b* to correspond to screw holes 409 of bone plate 401.

Figure 5:
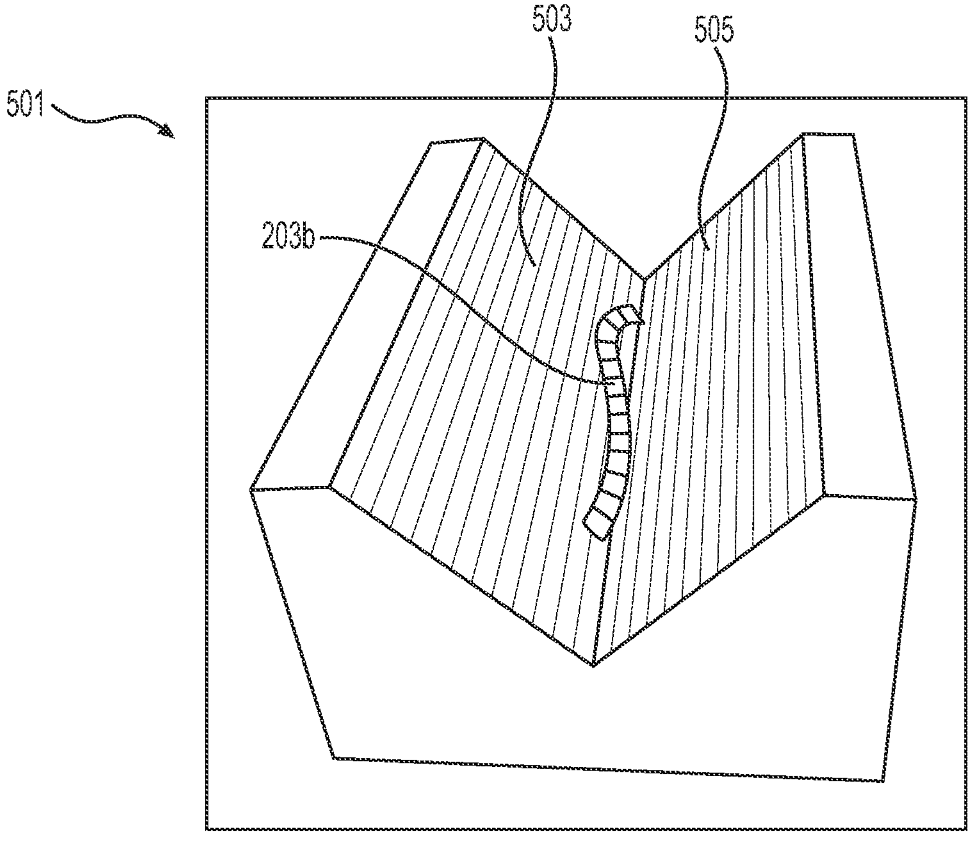
FIG. 5 illustrates an image cradle according to some embodiments of inventive concepts.

After shaping template 203*b* based on the contour and length of the implant site as shown in FIG. 2B, template 203*b* may be placed in imaging cradle 501 with sides 503 and 505 that are 90 degrees perpendicular (orthogonal) as shown in FIG. 5. These perpendicular surfaces 503 and 505 may have horizontal and/or vertical reference lines or other markings to facilitate image analysis by providing information about scaling and orientation of template 203*b*. With its V-shaped trough, imaging cradle 501 may enable complimentary imaging of template 203*b* at orthogonal angles, as shown in FIG. 6.

Figure 6:
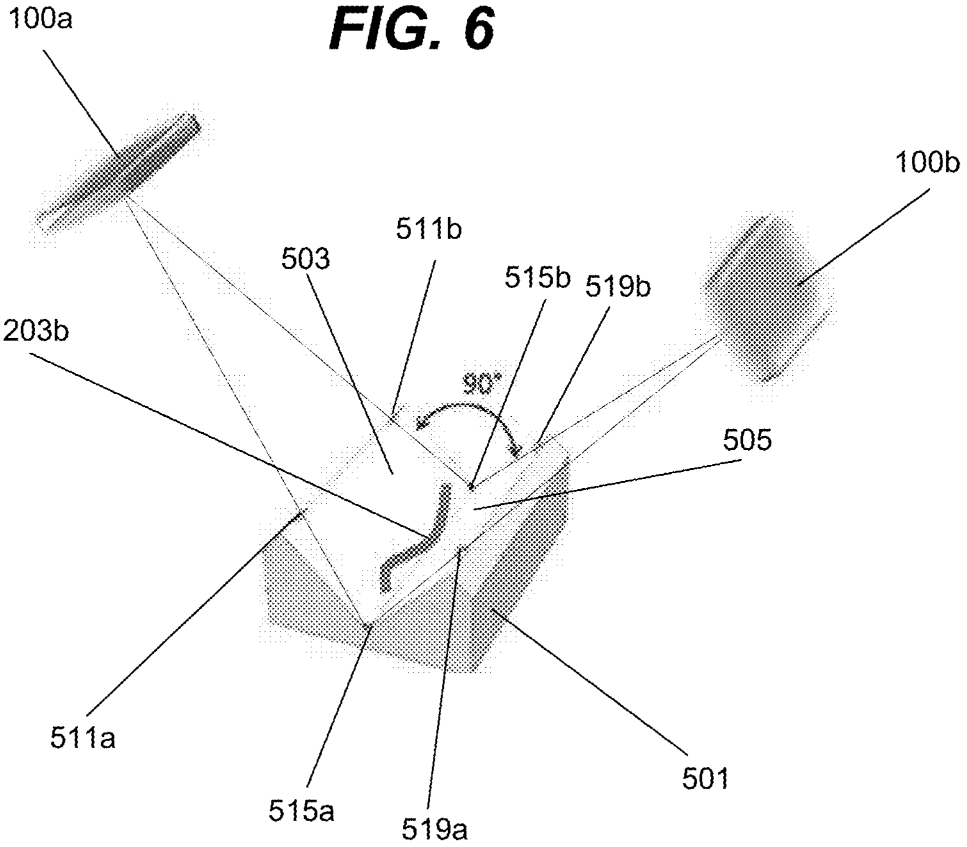
FIG. 6 is a diagram illustrating an image cradle using two camera positions according to some embodiments of inventive concepts.

The orthogonal images of template 203*b* may be captured with camera 107 of selection device 100 of FIG. 1 from positions 100*a* and 100*b* as shown in FIG. 6. As discussed above, selection device 100 may be implemented using a smart phone, a tablet computer, or other similar device with on-board software. According to some other embodiments, the orthogonal images may be captured by a camera or other imaging device outside selection device 100, and the orthogonal images (or data relating thereto) may be provided through wired/wireless interface 109 of selection device 100 to processor 103. Center position and/or focal distance may be calibrated using aligning markers 511*a-b*, 515*a-b*, and 519*a-b* on image cradle 501. The angle of 90 degree projection images may be assisted using gyroscopic and/or accelerometer feedback that may be commonly available in smart phone devices used as selection device 100.

Figure 7A:
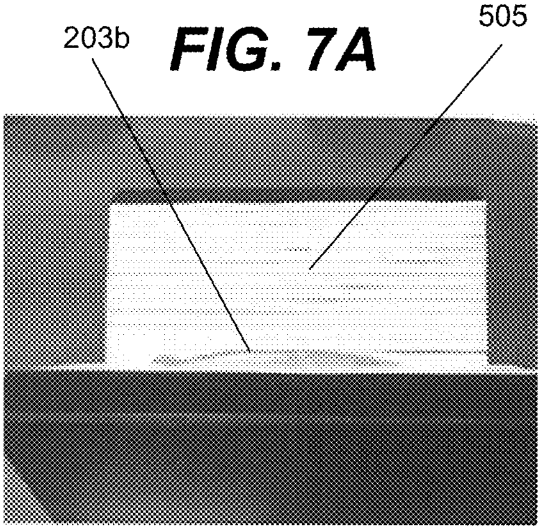
FIGS. 7A and 7B illustrate orthogonal images of a template taken using the image cradle of FIG. 6 according to some embodiments of inventive concepts.
Figure 7B:
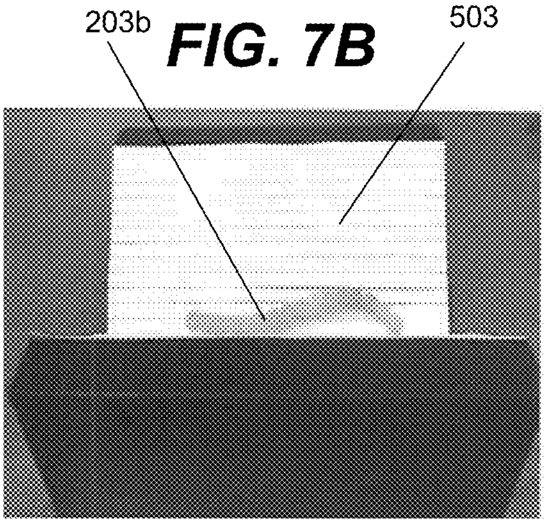

As shown in FIG. 6, selection device 100 including camera 107 may be held in positions 100*a* and 100*b* to take the respective images of FIGS. 7A and 7B. By aligning markers 511*a* and 515*a* and markers 511*b* and 515*b* in the image taken from position 100*a* and by aligning markers 519*a* and 515*a* and markers 519*b* and 515*b* in the image taken from position 100*b*, desired orientations of the orthogonal images may be provided. As discussed above, one camera 107 from selection device 100 (or one camera outside of selection device 100) may be used to take the orthogonal images of FIGS. 7A and 7B from positions 100*a* and 100*b*. According to some other embodiments, separate cameras may be mounted (permanently or detachably) in positions 100*a* and 100*b* to take the images of FIGS. 7A and 7B without requiring manual alignment. An image capture device, for example, may include imaging cradle 501 and two cameras that are mounted in positions 100*a* and 100*b* to capture the images of FIGS. 7A and 7B, and the resulting images (or data such as dimensional parameters relating thereto) may be provided to selection device 100 through wired/wireless interface 109.

FIG. 8A shows a view of imaging cradle 501 taken from camera position 101*b* with alignment markers 515*a-b* and 519*a-b*. FIG. 8B shows alignment of markers 515*a* and 519, and FIG. 8C shows alignment of markers 515*b* and 519*b* as will occur when the camera is properly aligned at position 101*b*. Once the alignment of FIGS. 8B and 8C has been achieved, the image can be taken with assurance that the camera is properly positioned. If either of markers 515*a* and 519*a* or markers 515*b* and 519*b* is out of alignment after taking the image, processor 103 may reject the image and generate a request (provided through a screen/display and/or speaker of user interface 101) for the user to retake the image. According to some embodiments, processor 103 may use such visual misalignment from markers 515*a*, 519*a*, 515*b*, and/or 519*b* to adjust the image and/or data derived therefrom.

As shown in FIG. 9, a mirror 521 (or multiple) may be added to image cradle 501 to enable two (or more) projection angles to be captured by camera 107 of selection device 100 with one image from one angle. Mirror 521 may be a non-reversing mirror. Position and distance may again be calibrated with markers on the cradle as discussed above with respect to FIGS. 8A-C. Use of mirror 521 may allow the orthogonal images of template 203*b* to be captured in one photo instead of two. Here, the one image may include both a direct image of template 203*b* corresponding to the image of FIG. 7B and a reflection 203*b*' of template 203*b* corresponding to the image of FIG. 7A. As discussed above, camera 107 of selection device 100 may be used in FIG. 9, or a separate camera may be used with the image or data relating thereto being provided to processor 103 through wired/wireless interface 109. According to some other embodiments, a separate camera may be mounted with respect to cradle 501 to maintain a desired alignment.

In addition to a camera in a hand-held device, a head-mounted camera worn by the surgeon may be used to capture the shape of template 203*b*. A tracking system associated with such a head-mounted camera may provide a pose/orientation of the head-mounted camera relative to the imaging cradle 501 or holder for the implant and can provide/ensure that frames for analysis are captured at 90° or any desired angle for analysis.

In addition to or instead of a deformable template, the surgeon could place visual markers (such as reflective fiducial markers) at the anatomical site (e.g., on the exposed bone surface). Reflective fiducial markers could be tracked stereophotogrammetrically using tracking cameras, and their locations detected in 3D (3-dimensional) space. These 3D surface points could be analyzed similarly to template points and used by processor 103 to select the appropriate implant.

According to some other embodiments, surgical ink may be used wherein the surgical ink has a property/properties that cause it to selectively adhere to bone and not to surrounding soft tissue. Such ink could be detectable using visual tracking or could be radio-opaque, detectable using x-rays. Photos or radiographs of the bone with adhered ink could be processed by processor 103 to detect the bone surface contours. Selected points along the contours could be analyzed by processor 103 similarly to template points to select an appropriate implant.

Regardless of the method used to determine points on the surface of the bone where the implant is intended to rest, fitting operations discussed below may be used by processor 101.

Figure 10A:
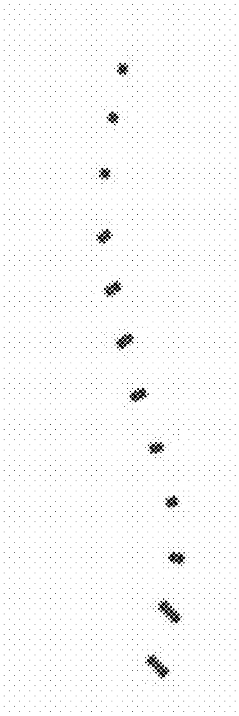
FIGS. 10A and 10B illustrate lines generated using auto-detection from different images of a template according to some embodiments of inventive concepts.
Figure 10B:
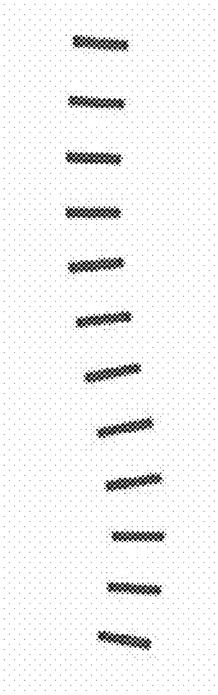
Figure 11A:
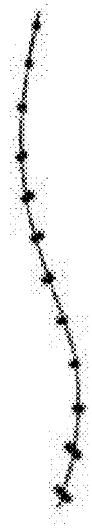
FIGS. 11A and 11B illustrate a fitting of splines using lines of FIGS. 10A and 10B according to some embodiments of inventive concepts.
Figure 11B:
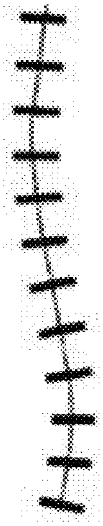

Image analysis may then be performed by processor 103 using the images of FIGS. 7A and 7B, or using the combined image resulting from FIG. 9 (or using other images or related data). In embodiments using a smartphone to implement selection device 100, a software application on the device (e.g., an Android app, an iOS app, etc.) may use operations to auto-detect the lines 209 on each segment of template 203*b*, in each projection (e.g., in the images of FIGS. 7A and 7B). By corresponding lines 209 with projections, processor 103 may map lines 209 to 3D space. FIG. 10A illustrates an example of processor 103 autodetecting lines 209 from the image of template 203*b* in FIG. 7A, and FIG. 10B illustrates an example of processor 103 autodetecting lines 209 from the image of template 203*b* in FIG. 7B. Processor 103 may then fit a spline through the midpoint of each line 209 as shown in FIGS. 11A and 11B.

Using the app, processor 103 may then generate prompts for questions relevant to the surgical procedure, such as anatomical placement (e.g., superior vs anterior). Processor 103, for example, may provide the prompts/questions visually through a touch screen or other display of user interface 101 and/or audibly through a speaker of user interface 101. Using the app, processor 103 may follow a best-fit algorithm to match the spline that is associated with template 203*b* or other method of surface geometry detection with a library or lookup table of splines corresponding to sizes/curvatures of implants available for the procedure. Using the app, processor 103 may then provide a recommendation to the user (e.g., surgeon) regarding the implant with the best-fitting spline. The recommendation may include an identification of the selected implant (e.g., a part number), a quantitative closeness of fit (e.g., 0% to 100%), and/or next-best alternatives. Using the app, processor 103 may also suggest where to bend the implant for a better fit, such as between two specific screw holes. Processor 103 could provide (on a display such as touch screen 101*c* or an external monitor) a graphic of the selected plate overlaid on a graphic of the template with arrows indicating where and how much to bend the plate to achieve a better fit. The recommendation(s) may be provided visually through a touch screen or other display of user interface 101 and/or audibly through a speaker of user interface 101.

Another embodiment may use the bending template to define and apply all necessary bending to a straight plate. That is, the curvature defined by the template and read from the optical or other sensing algorithm would then be applied to a straight plate either manually or automatically.

If using the system to apply bending to a straight plate through a manual process, the processor 103 could provide (on a display such as touch screen 101*c* or an external monitor) a graphic of the desired curvature with arrows indicating locations and magnitudes of necessary bends. Processor 103 could also show an actual size "blueprint" of the plate in its final form that could be printed or shown actual size on a monitor. The system could also assist the surgeon or technician in determining whether starting from a straight plate is a better decision than starting from a pre-bent plate and further bending the plate or back-bending it. During manual bending, the surgeon or technician could periodically hold the plate up to the template to check whether the desired curvature was achieved. Such an on-screen template might be a better visual guide for the surgeon than the physical template that was laid on bone because it may have thickness, hole spacing and general appearance more similar to the actual plate than the template itself.

If using the system to apply bending to a straight plate through an automatic process, processor 103 could electronically feed information on the locations and magnitudes of bends through wired/wireless interface to an automatic bending device. The bending device would activate a bending mechanism that could include computer-controlled rollers, clamps, and/or actuators that would apply the desired bending to the straight plate so that it best matches the template.

Use of selection device 101 and/or methods thereof may thus automate implant selection during surgery. Using such automation may reduce human error, for example, due to a surgeon overlooking and/or misjudging a best-fitting implant, and using such automation may provide quantitative evaluation to augment subjective human judgment.

Moreover, it may be difficult for a surgeon to visually assess relative fits of different implants sitting in a case, and it may be impractical to try all of them. For example, each implant that is tried but not used may be thereafter unusable due to contamination from contact to the implant site. Virtual fitting of implants according to methods/devices herein may spare unused implants from unnecessary contamination at the surgical site, thereby reducing waste. Moreover, assisted implant selection using methods/devices herein may also reduce the time of the procedure, thereby reducing time that the patient is under anesthesia, benefitting both the surgical team and patient. By improving initial selection of the implant, bending of implants to fit the patient's anatomy may be reduced. Because excessive bending of an implant may weaken the implant, a reduction in bending may reduce a risk of implant failure.

Methods, devices, and computer program products discussed herein may thus provide a combination of speed of selection and initial accuracy of fit that is not attainable using manual selection. Such speed and accuracy can reduce the time required for surgery, reduce the time that a patient is subject to anesthesia, improve a fit of the implant, and improve the ultimate patient outcome. Moreover, by providing coordinates incrementally for both the template and for the available implants, an efficiency of the comparisons may be improved thereby improving an efficiency of operations of processor 103 to improve a computer-related technology.

According to some embodiments, clavicle plate (also referred to as an implant) selection software may be provided using a Windows-based interface or a smartphone/tablet app. Image processing may include detecting curvature of template 203*b* (also referred to as a plate surrogate) in 2 planes and extracting the 3D shape parameters for comparison to a database of implant shapes/sizes. VTK, Qt, Open-CV and other open-source options may be used by processor 103 to detect colors and contours from photo images. Moreover, a Structured Query Language SQL database may be used to store a library of information regarding shapes, dimensions, etc., regarding the available implants. Such a database may be stored in memory 105 of selection device 100, or the database may be stored external to selection device 100 with processor 103 accessing information from the database through wired/wireless interface 109.

Upon receiving images of FIGS. 7A and 7B, for example, processor 103 may automatically process and reorient the images using alignment marks, because orientations of the images from different cameras (of different types) cannot be guaranteed and because there may be uncertainty due to variations in how the user holds the device while taking the photo(s). Alignment marks according to some embodiments are discussed above with respect to FIGS. 6, 8A-C, and 9. According to some other embodiments, alignment may be provided using marks illustrated in FIG. 12.

Figure 12:
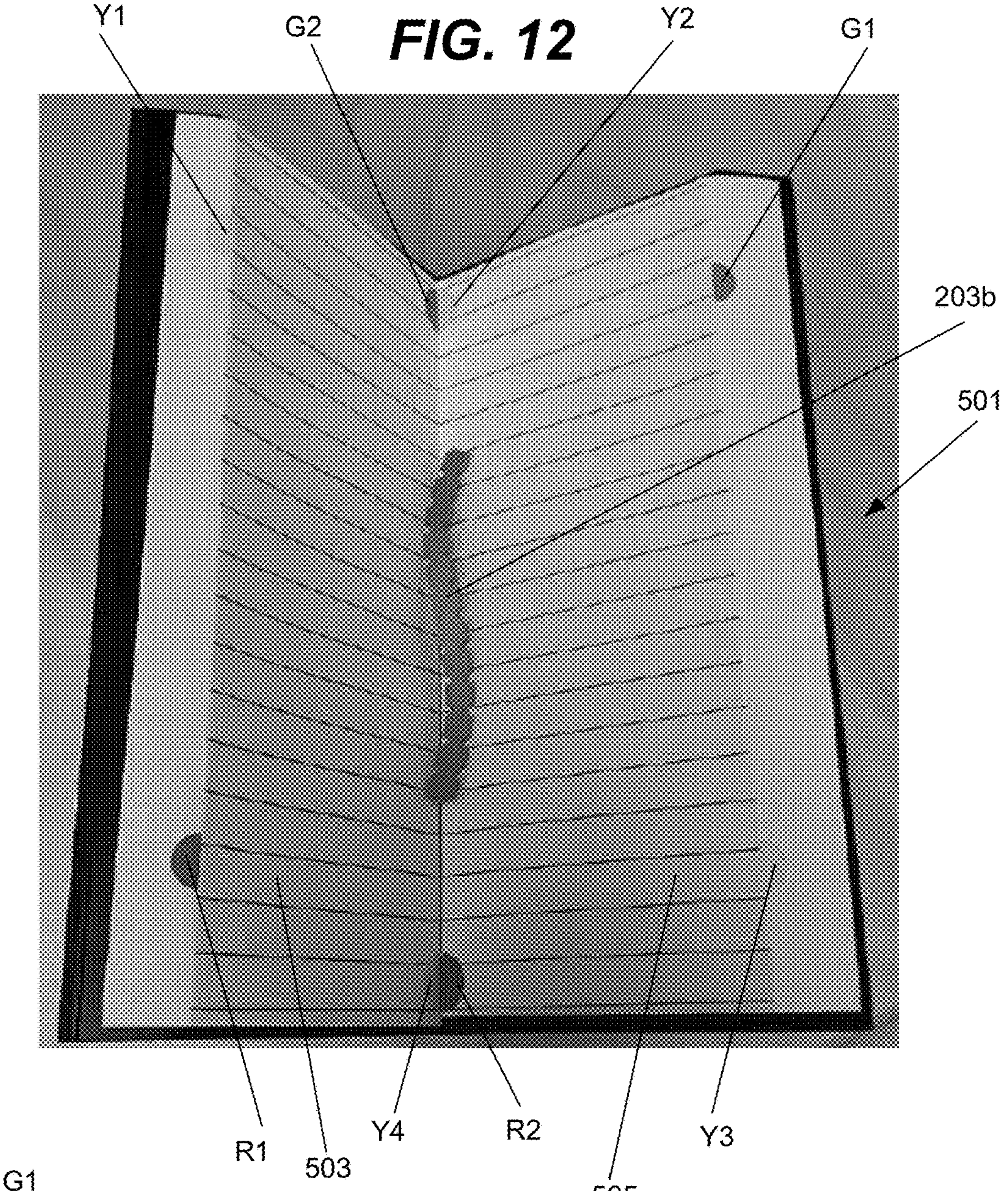
FIG. 12 illustrates a template in an image cradle including alignment markers according to some embodiments of inventive concepts.

As shown in FIG. 12, alignment marks G1 and G2 and alignment marks Y3 and Y4 may be used for one image of template 203*b*, and alignment marks Y1 and Y2 and alignment marks R1 and R2 may be used for another image of template 203*b*. These different colored alignment marks may be used to specify left-right-up-down, and these markings may be autodetected by processor 103 using Open-CV color masking operations. The alignment marks of FIG. 12 may also be used to distinguish a series of shots from one another to reduce/prevent accidental loading of duplicate shots instead of a valid pair. To distinguish the shots, one side of image cradle 501 may display yellow and green alignment marks (half circles that form circular dots when properly aligned), and the other side of image cradle 501 may display yellow and red alignment marks (half circles that form circular dots when properly aligned). As further shown in FIG. 12, lines may extend from the intersection of the two sides 503 and 505, for example, to provide scale.

Figure 13:
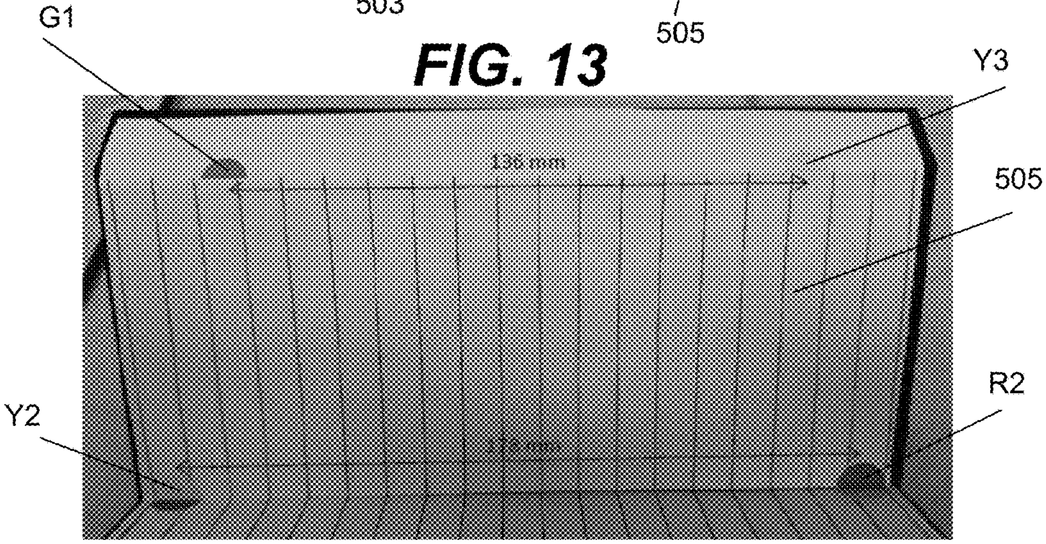
FIG. 13 illustrates different spacings of alignment markings from the image cradle of FIG. 12 according to some embodiments of inventive concepts.
Figure 14A:
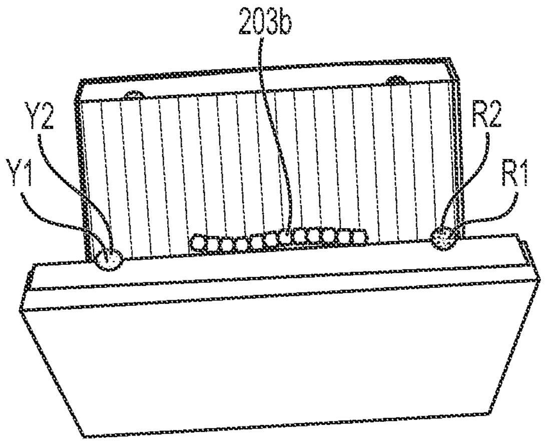
FIGS. 14A and 14B illustrate orthogonal images of a template in an image cradle using alignment markers of FIGS. 12 and 13 according to some embodiments of inventive concepts.
Figure 14B:
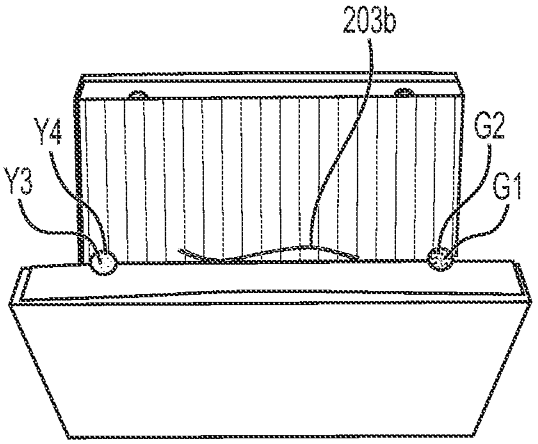

As shown in the view of FIG. 13, half circles at the intersection of the sides (e.g., Y2 and R2 may be spaced apart by 178 mm, and half circles at the top of cradle 501 (e.g., G1 and Y3) may be spaced apart by 136 mm. Moreover, half circles at the top of cradle 501 (e.g., G1 and Y3) may have a smaller diameter than half circles at the intersection of sides (e.g., Y2 and R2) because the half circles at the intersection of sides (e.g., Y2 and R2) will be further from the camera when alignment is performed and the image is taken. Alignment using this arrangement of alignment half circles may facilitate/force the user to take photos from a distance of about 35 cm from template 203*b*. Having this focal distance as a known value while inter-dot distance is also known may allow scaling of pixels to millimeters. Additionally, the known spacing of vertical blue lines may be 1.0 cm to provide a secondary check of the scaling. This information can be used to determine a length of template 203*b*. FIGS. 14A and 14B provide the resulting orthogonal images of template 203*b* taken using image cradle 501 with the alignment markers of FIG. 12.

Figure 15A:
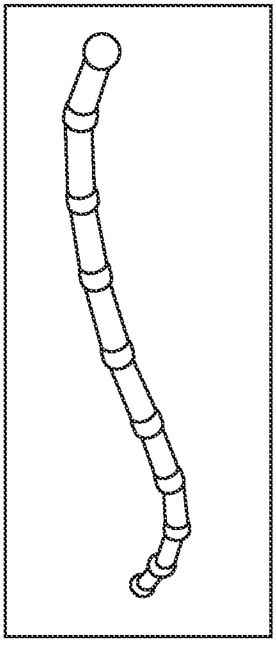
FIGS. 15A, 15B, and 15C are screenshots illustrating renderings of a spline according to some embodiments of inventive concepts.
Figure 15B:
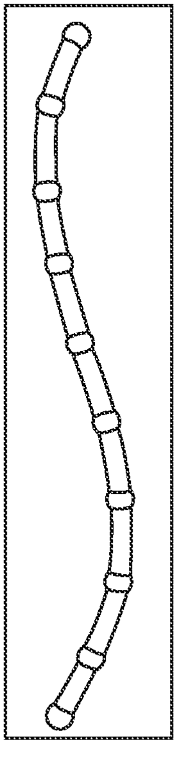
Figure 15C:
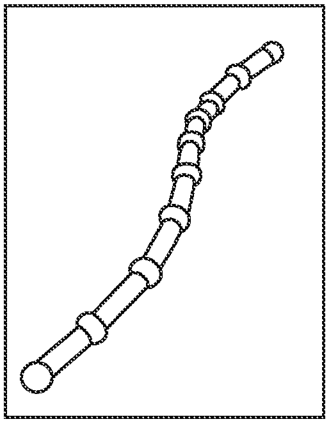

After processor 103 has processed the images of FIGS. 14A and 14B to identify segment locations, processor 103 may join the segment locations together and fit the segment locations with a spline. Processor 103 may calculate and render splines, for example, using VTK. FIGS. 15A, 15B, and 15C are screenshots showing a spline of 10 points joined together with a cylinder. According to some embodiments, it may be possible to grab each white spherical handle with a left mouse click and drag to adjust its position. It may also be possible to change the perspective view by clicking and dragging on the screen anywhere other than handle locations. In the app, processor 103 may adjust handle positions to modify a fit factor and also possibly the selection of best-fitting plate. Accordingly, it may be a useful feature to enable the user (surgeon) to proactively explore possibilities for plates/implants. For example, if the user makes the end of the plate a little more curvy, processor 103 may suggest a different plate.

According to additional embodiments, processor 103 may render images on a display of user interface 101 as flat strips joined by spheres instead of cylinders to represent actual plates. Moreover, processor 103 may only allow the user to move handles laterally on the display while keeping the longitudinal spacing between handles constant to facilitate easier comparison of the spline with a database of implant splines. Processor 103 may also use a data structure for passing spline points to code that compares the spline points to stored splines in a database.

Figure 16A:
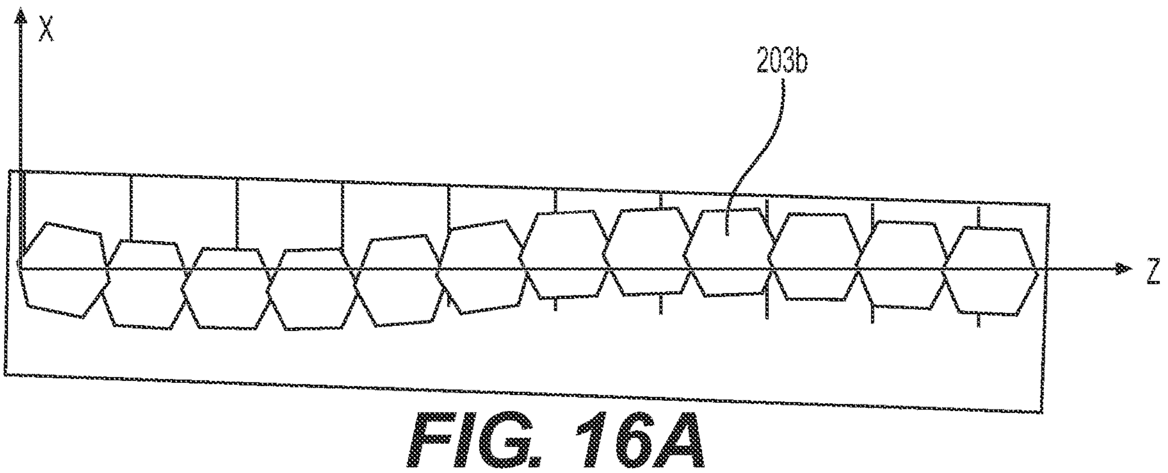
FIGS. 16A and 16B illustrate transformations of a template oriented on a z-axis according to some embodiments of inventive concepts.
Figure 16B:
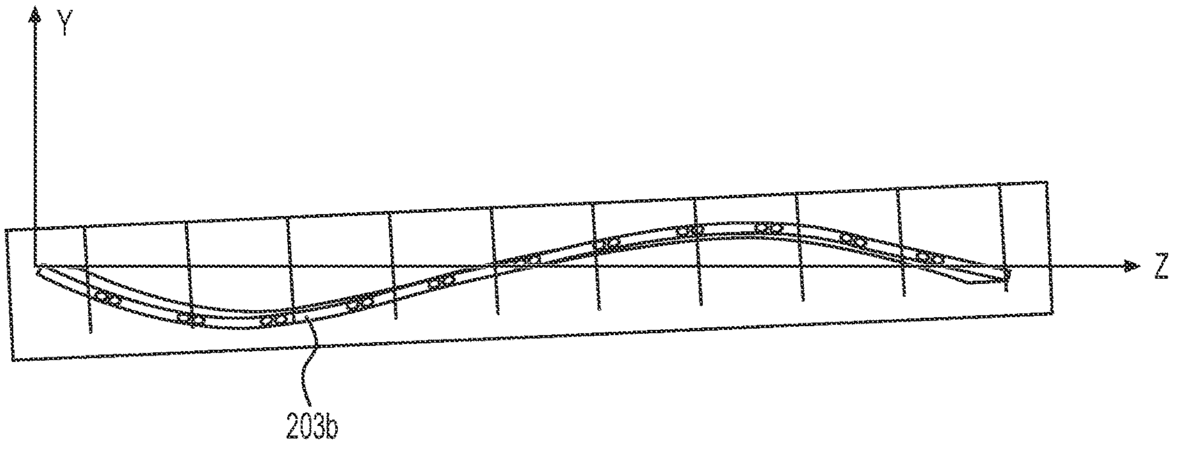

Moreover, different layouts may be provided for the database of implants. One configuration may orient the found plate shape from template 203*b* such that the starting end is at (xs,ys,zs)=(0,0,0) and the opposite end is at (xf,yf,zf)=(0,0,zf) as shown in FIGS. 16A and 16B. That is, processor 103 may spatially transform the shape to orient it along the z axis. Then, processor 103 may rotate the shape to place it with the flat surface of the plate parallel to the xz plane and perpendicular to the yz plane, with dorsal direction toward +y and ventral direction toward −y. This configuration is shown in FIGS. 16A and 16B.

Processor 103 may then evaluate x,y values of the template at fixed increments of z and compare these x,y values against x,y values stored in the database for the different available implants. The z increment should be fine enough to capture the curvature of the plate without having to store an excessive number of values. For example, 5 mm increments may be used. Since plates may have different lengths (in addition to different curves/contours), the number of entries evaluated and compared may depend on the desired plate length. Table 1 below shows an example for a 50 mm plate. In this example, processor 103 may query the database and measure the average vector distance from the measured 9 incremental points (i.e., points 2-10) relative to each the corresponding points stored in database entries for plates with matching length (or close to the same length). The smallest mean would be the best matching plate. This mean value would also provide a gauge of goodness of fit.

TABLE 1

Measured data for template/implants.

| Point | X | Y | Z |
|---|---|---|---|
| 1 | 0 | 0 | 0 |
| 2 | X2 | Y2 | 5 |
| 3 | X3 | Y3 | 10 |
| 4 | X4 | Y4 | 15 |
| 5 | X5 | Y5 | 20 |
| 6 | X6 | Y6 | 25 |
| 7 | X7 | Y7 | 30 |
| 8 | X8 | Y8 | 35 |
| 9 | X9 | Y9 | 40 |
| 10 | X10 | Y10 | 45 |
| 11 | 0 | 0 | 50 |

Figure 17:
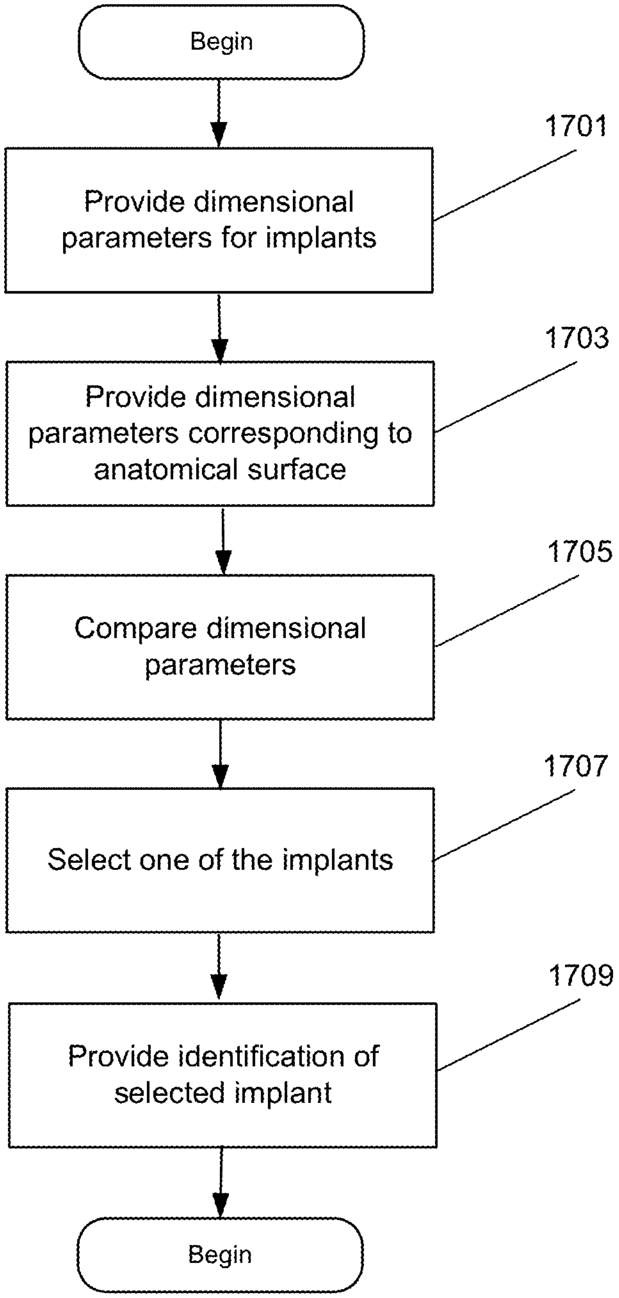
FIG. 17 is a flow chart illustrating operations of a selection device according to some embodiments of inventive concepts.

Operations of selection device 100 to identify a medical implant (e.g., a bone plate) from a plurality of medical implants will now be discussed with reference to the flow chart of FIG. 17.

At block 1701, processor 103 may provide dimensional parameters for each of the plurality of medical implants. Providing the dimensional parameters for each of the plurality of medical implants may include providing access to a stored database of the dimensional parameters that define a shape/dimensions for each of the respective medical implants of the plurality of medical implants. The stored database may be provided in memory 105 of selection device 100, or the stored database may be provided outside of selection device 100 with processor 103 accessing the stored database through wired/wireless interface 109. The stored database, for example, may include a table of points for each available implant as discussed above with respect to Table 1, such that dimensional parameters for each of the plurality of medical implants include coordinate values (e.g., x and y coordinate values) corresponding to increments along each of the medical implants (e.g., along the z-axis).

At block 1703, processor 103 may provide dimensional parameters corresponding to an anatomical surface (e.g., a surface of a bone) to which the implant is to be fixed. The dimensional parameters corresponding to the anatomical surface, for example, may include a table of points as discussed above with respect to Table 1, such that dimensional parameters corresponding to the anatomical surface include coordinate values (e.g., x and y coordinate values) corresponding to increments along the anatomical surface (e.g., along the z-axis). The dimensional parameters corresponding to the anatomical surface may be provided based on digital image data including first and second digital images that are different. Moreover, the digital image data may be taken from a template representing the anatomical surface, or the digital image data is taken from the anatomical surface (directly). Selection device 100, for example, may include camera 107 that captures digital images to be processed by processor 103 to generate the dimensional parameters. According to some other embodiments, images may be captured outside of selection device 100, received by processor 103 through wired/wireless interface 109, and processed by processor 103 to generate the dimensional parameters. According to still other embodiments, images may be captured outside selection device 100, the images may be processed outside of selection device 100 to generate the dimensional parameters, and the dimensional parameters may be received by processor 103 through wired/wireless interface 109.

At block 1705, processor 103 may compare the dimensional parameters for each of the plurality of medical implants with the dimensional parameters corresponding to the anatomical surface. For example, processor 103 may compare coordinate values (e.g., x-y coordinate values taken at increments along a z-axis) corresponding to the plurality of medical implants with coordinate values (e.g., x-y coordinate values taken at increments along a z-axis) corresponding to the anatomical surface. For such a comparison, processor 103 may determine differences between the coordinate values corresponding to the anatomical surface and respective ones of the coordinate values corresponding to each of the plurality of medical implants.

At block 1707, processor 103 may select one of the medical implants from the plurality of medical implants based on comparing the dimensional parameters for each of the plurality of medical implants with the dimensional parameters corresponding to the anatomical surface. Processor 103, for example, may select the one of the medical implants having a least average difference between the coordinate values corresponding to the anatomical surface and the coordinate values corresponding to the one of the medical implants that is selected.

At block 1709, processor 103 may provide an identification of the medical implant selected from the plurality of medical implants through user interface 101. The identification of the selected medical implant, for example, may be provided visually through a display (e.g., touch screen 101*c*) of user interface 101 and/or audibly through speaker 101*d* of user interface 101. The identification may include a name, a part number, a size, etc. In addition, processor 101 may provide additional information (visually or audibly), such as a recommended location to bend the selected implant.

As discussed above according to some embodiments, the dimensional parameters corresponding to the anatomical surface may be provided at block 1703 based on digital image data including first and second digital images that are different, with the first and second digital images being taken from template 203*b* representing the anatomical surface as shown, for example, in FIGS. 14A and 14B.

The first and second digital images, for example, may be taken of template 203*b* in image cradle 501 that includes first alignment markers (Y1, Y2, R1, and R2) for the first digital image and second alignment markers (Y3, Y4, G1, and G2) for the second digital image as discussed above, for example, with respect to FIGS. 12, 13, 14A, and 14B. Based on the images of FIGS. 14A and 14B, processor 103 may provide the dimensional parameters corresponding to the anatomical surface at block 1703 responsive to verifying alignment of the first digital image of FIG. 14A based on the first alignment markers (Y1, Y2, R1, and R2) and responsive to verifying alignment of the second digital image of FIG. 14B based on the second alignment markers (Y3, Y4, G1, and G2).

As discussed above, the first and second digital images of FIGS. 14A and 14B may be taken of template 203*b* in cradle 501 that includes first alignment markers (Y1, Y2, R1, and R2) for the first digital image and second alignment markers (Y3, Y4, G1, and G2) for the second digital image. At block 1703, processor 103 may use alignment markers for a digital image to determine alignment/misalignment of the image and either accept an image that is aligned, or reject an image that is misaligned and request that the user (surgeon) retake the rejected image. Processor 103, for example, may provide the dimensional parameters corresponding to the anatomical surface at block 1703 using the following operations. Responsive to first user input, a first version of the first digital image of FIG. 14A may be captured through camera 107 including template 203*b* in cradle 501 with first alignment markers (Y1, Y2, R1, and R2). Responsive to detecting misalignment of the first alignment markers in the first version of the first digital image of FIG. 14A, processor 103 may provide an instruction to retake the first digital image of FIG. 14A through the user interface 101 (e.g., a visual instruction through a display and/or an audible instruction through a speaker). Responsive to second user input after providing the instruction, a second version of the first digital image of FIG. 14A may be captured through camera 107 including template 203*b* in cradle 501 with the first alignment markers. Responsive to third user input, the second digital image of FIG. 14B may be captured through camera 107 including template 203*b* in cradle 501 with the second alignment markers. Responsive to the second version of the first digital image of FIG. 14A being aligned based on alignment markers (Y1, Y2, R1, and R2) and the second digital image of FIG. 14B being aligned based on alignment markers (Y3, Y4, G1, and G2), processor 103 may provide the dimensional parameters corresponding to the anatomical surface based on the second version of the first digital image and the second digital image. Either image may be rejected any number of times until each image is captured with proper alignment.

As discussed above, the first and second digital images of FIGS. 14A and 14B may be taken of template 203*b* in cradle 501 that includes first alignment markers (Y1, Y2, R1, and R2) for the first digital image and second alignment markers (Y3, Y4, G1, and G2) for the second digital image. Processor 103 may provide the dimensional parameters corresponding to the anatomical surface based on the at least one of the first alignment markers and/or the second alignment markers. Processor 103, for example, may use an alignment/misalignment of the alignment markers to determine a camera distance from cradle/template 501/203*b*, a camera angle relative to cradle/template 501/203*b*, and/or other information that may be used to determine dimensional parameters corresponding to the anatomical surface.

According to some other embodiments, processor 103 may the dimensional parameters corresponding to the anatomical surface based on digital image data including first and second digital images that are different, wherein the first and second digital images are taken from the anatomical surface (directly). Such images may be taken either before or during the operation, and the digital image data may include at least one of x-ray image data, computed tomography image data, ultrasound image data, magnetic resonance image data, and/or photographic image data.

According to some embodiments, providing dimensional parameters corresponding to the anatomical surface at block 1703 may include providing a curve (e.g., a spline) to represent a shape of the anatomical surface, and selecting at block 1707 may include selecting the one of the medical implants to match the shape of the anatomical surface based on the curve.

Further Definitions and Embodiments are discussed below.

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a “circuit,” “module,” “component,” or “system.” Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the “C” programming language, Visual Basic, Fortran 2003, Perl, COBOL 2002, PHP, ABAP, dynamic programming languages such as Python, Ruby and Groovy, or other programming languages. The program code may execute entirely on the user’s computer, partly on the user’s computer, as a stand-alone software package, partly on the user’s computer and partly on a remote computer or entirely on the remote computer or server. In the latter scenario, the remote computer may be connected to the user’s computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer processor, other programmable data processing apparatus, or other devices to function in a particular manner, such that the instructions when stored in the computer readable medium produce an article of manufacture including instructions which when executed, cause a computer processor to implement the function/act specified in the flowchart and/or block diagram block or blocks. The computer program instructions may also be loaded onto a computer processor, other programmable instruction execution apparatus, or other devices to cause a series of operational steps to be performed on the computer, other programmable apparatuses or other devices to produce a computer implemented process such that the instructions which execute on the computer processor or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being “connected”, “coupled”, “responsive”, or variants thereof to another element, it can be directly connected, coupled, or responsive to the other element or intervening elements may be present. In contrast, when an element is referred to as being “directly connected”, “directly coupled”, “directly responsive”, or variants thereof to another element, there are no intervening elements present. Like numbers refer to like elements throughout. Furthermore, “coupled”, “connected”, “responsive”, or variants thereof as used herein may include wirelessly coupled, connected, or responsive. As used herein, the singular forms “a”, “an” and “the” are intended to include the plural forms as well, unless the context clearly indicates otherwise. Well-known functions or constructions may not be described in detail for brevity and/or clarity. The term “and/or” includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms “a”, “an” and “the” are intended to include the plural forms as well, unless the context clearly indicates otherwise. It will be further understood that the terms “comprise”, “comprising”, “comprises”, “include”, “including”, “includes”, “have”, “has”, “having”, or variants thereof are open-ended, and include one or more stated features, integers, elements, steps, components or functions but do not preclude the presence or addition of one or more other features, integers, elements, steps, components, functions or groups thereof. As used herein, the term “and/or” includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain principles of the disclosure and practical applications, and to enable others of ordinary skill in the art to understand the disclosure with various modifications as are suited to the particular use contemplated.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following claims and their equivalents, and shall not be restricted or limited by the foregoing detailed description.

The invention claimed is:

1. A method of a selection device for identifying a bone plate implant from a plurality of bone plate implants to be fixed to an anatomical surface, the method comprising:

providing a three dimensional contour corresponding to the anatomical surface based on digital image data taken from a template representing the anatomical surface of a particular patient;

wherein the template includes markings to facilitate image recognition and provided on only one of two primary faces of the template to ensure proper orientation of the template, wherein the three dimensional contour corresponding to the anatomical surface is prepared by templating, imaging and image analysis;

receiving by a processor of the selection device the provided three dimensional contour;

comparing, by the processor of the selection device, the received three dimensional contour of the anatomical surface of the particular patient against stored three dimensional contours of a plurality of bone plate implants for optimal fit, the stored three dimensional contour including a shape of the bone plate implant;

selecting, by the processor of the selection device, one of the bone plate implants from the plurality of bone plate implants based on the comparison of the optimal fit;

providing, by the processor of the selection device, an identification of the selected bone plate implant through a user interface.

2. The method of claim 1, further comprising providing access to a database storing the three dimensional contours of a plurality of bone plate implants that define the shape for each of the respective implants of the plurality of bone plate implants.

3. The method of claim 2, wherein providing access comprises providing a curve to represent a shape of the anatomical surface, and wherein selecting comprises selecting the one of the implants to match the shape of the anatomical surface based on the curve.

4. The method of claim 1, wherein the three dimensional countour for each of the plurality of implants include coordinate values corresponding to increments along each of the implants, the method further comprising providing coordinate values corresponding to increments along the anatomical surface, and wherein comparing comprises comparing the coordinate values corresponding to the plurality of implants with the coordinate values corresponding to the anatomical surface.

5. The method of claim 4, wherein comparing comprises determining differences between the coordinate values corresponding to the anatomical surface and respective ones of the coordinate values corresponding to each of the plurality of implants, and wherein selecting comprises selecting the one of the implants having a least average difference between the coordinate values corresponding to the anatomical surface and the coordinate values corresponding to the one of the implants that is selected.

6. The method of claim 1, wherein the first and second digital images are taken from the template positioned in a cradle that includes first alignment markers for the first digital image and second alignment markers for the second digital image, and wherein providing the three dimensional contour corresponding to the anatomical surface comprises providing the dimensional parameters corresponding to the anatomical surface based on the first and second digital images responsive to verifying alignment of the first digital image based on the first alignment markers and responsive to verifying alignment of the second digital image based on the second alignment markers.

7. The method of claim 1, wherein the first and second images are taken from the template positioned in a cradle including first alignment markers for the first digital image and second alignment markers for the second digital image, wherein providing the three dimensional contour line corresponding to the anatomical surface comprises:

responsive to first user input, capturing a first version of the first digital image including the template in the cradle with the first alignment markers, responsive to misalignment of the first alignment markers in the first version of the first digital image, providing an instruction to retake the first digital image through the user interface, responsive to second user input after providing the instruction, capturing a second version of the first digital image including the template in the cradle with the first alignment markers, responsive to third user input, capturing the second digital image including the template in the cradle with the second alignment markers, and providing the three dimensional contour corresponding to the anatomical surface based on the second version of the first digital image and the second digital image.

8. The method of claim 1, wherein the first and second digital images are taken of the template in a cradle that includes first alignment markers for the first digital image and second alignment markers for the second digital image, and wherein providing the three dimensional contour corresponding to the anatomical surface comprises providing the dimensional parameters corresponding to the anatomical surface based on the at least one of the first alignment markers and/or the second alignment markers.

9. The method of claim 1, wherein the digital image data is taken from the anatomical surface.

10. The method of claim 9, wherein the digital image data comprises at least one of x-ray image data, computed tomography image data, ultrasound image data, magnetic resonance image data, and/or photographic image data.

11. The method of claim 1, wherein the anatomical surface is a surface of a bone.

12. A computer program product, comprising:

a tangible computer readable storage medium comprising computer readable program code embodied in the medium that when executed by a processor causes the processor to perform operations comprising:

providing a three dimensional contour corresponding to the anatomical surface of a particular patient based on digital image data taken from a template representing the anatomical surface;

wherein the template includes markings to facilitate image recognition and provided on only one of two primary faces of the template to ensure proper orientation of the template;

wherein the three dimensional contour corresponding to the an anatomical surface is prepared by templating, imaging and image analysis;

receiving by the processor the provided three dimensional contour;

comparing the received three dimensional contour of the anatomical surface of the particular patient against stored three dimensional contour of a plurality of bone plate implants for optimal fit, the stored three dimensional contour including a shape of the bone plate implant;

selecting one of the bone plate implants from the plurality of bone plate implants based on the comparison of the optimal fit;

providing an identification of the selected bone plate implant through a user interface.

* * * * *